United States Patent [19]
Lesniak

[11] Patent Number: 6,109,780
[45] Date of Patent: Aug. 29, 2000

[54] DYNAMIC VORTEX IMPELLER

[75] Inventor: Andrew Paul Lesniak, Wilmington, Del.

[73] Assignee: S. P. Industries Inc., Buena, N.J.

[21] Appl. No.: 09/010,632

[22] Filed: Jan. 22, 1998

[51] Int. Cl.[7] ..................................................... B01F 7/16
[52] U.S. Cl. ........................ 366/253; 366/247; 366/307
[58] Field of Search ................................... 366/245, 246, 366/247, 273, 274, 307, 325.92, 342

[56] References Cited

U.S. PATENT DOCUMENTS

| | | |
|---|---|---|
| 1,032,663 | 7/1912 | Fay . |
| 1,101,199 | 6/1914 | Buechner . |
| 1,841,434 | 1/1932 | Gibson . |
| 2,025,378 | 12/1935 | Croasdale, Jr. ........................ 366/247 |
| 2,208,637 | 7/1940 | Jones et al. . |
| 2,572,375 | 10/1951 | Oertili . |
| 2,743,910 | 5/1956 | Melville . |
| 2,912,343 | 11/1959 | Collins et al. . |
| 3,113,228 | 12/1963 | Tolegian . |
| 3,245,665 | 4/1966 | Steel . |
| 3,622,129 | 11/1971 | Mazowski . |
| 3,888,466 | 6/1975 | Sedam ...................................... 366/274 |
| 4,162,855 | 7/1979 | Bender ..................................... 366/274 |
| 4,355,906 | 10/1982 | Ono . |
| 4,483,623 | 11/1984 | Eaton et al. ............................. 366/273 |
| 4,891,966 | 1/1990 | Kramer .................................. 366/307 |
| 5,074,671 | 12/1991 | Roueche et al. . |
| 5,167,449 | 12/1992 | Killough ................................. 366/273 |
| 5,183,336 | 2/1993 | Poltorak et al. ........................ 366/273 |
| 5,267,791 | 12/1993 | Christian et al. ....................... 366/247 |
| 5,407,270 | 4/1995 | Barile et al. . |

*Primary Examiner*—Tony G. Soohoo
*Attorney, Agent, or Firm*—Howson and Howson

[57] ABSTRACT

An apparatus and method of stirring cells in liquid culture media is provided. Baffles are mounted along the interior wall of the container and a hump is positioned on the center of the bottom surface of the container. A stirring apparatus is positioned inside the container. The blades of the stirring apparatus are angled outward toward the bottom of the container. The bottom edge of the blades extend closer to the bottom surface of the container then the apex of the hump. The liquid in the container is at a level below the top of the blades such that the blades are moved through the surface of the liquid. A magnetic bar is attached to the shaft and is driven by an external rotating magnetic bar.

18 Claims, 3 Drawing Sheets

DYNAMIC VORTEX IMPELLER

BACKGROUND OF THE INVENTION

This invention is related to the field of cell culture development systems. In particular, the invention is directed to a mixing apparatus and method which allows for the movement of cells in a liquid culture media both vertically and horizontally at a controlled rate, permitting adequate agitation and aeration of the culture media without damaging the cells. Further, the invention is directed to a lid design which creates a tight seal on various sized openings.

In various scientific fields, it is useful to grow cells in a culture media (such as a liquid suspension) over an extended period of time. However, increasing cell numbers results in the depletion of nutrients in the culture medium. When the media is allowed to stagnate, cell growth is inhibited and the cells can die. Any mixing device introduced to the culture media must be carefully selected and operated such that it does not damage the cells either by contaminating the culture media or by physically traumatizing the cells. Such a device must provide sufficient mixing such that nutrients are made available to most cells in the medium. Although innumerable mixing devices are known in other, unrelated and non-pertinent fields, they cannot be readily used or adapted to agitate cell cultures because they may create substantial stresses on the culture media, risking damage to the cells.

To overcome these problems, flasks have been developed which work in cooperation with stirring rods (or "spinners") to agitate the culture media and the cells. Typically, paddles are attached to the stirring rods, and are turned relatively slowly in the cultural media (about 5–150 rpm). While meeting with limited success, these devices generally fail to adequately agitate the cells. In particular, "dead spots" are created in the flasks in which portions of the liquid culture media are permitted to lie stagnant. These dead spots are most common along the sides and the bottom of the flask. Further, the flow created by these devices is generally laminar, both in horizontal bands and in vertical bands extending from the central axis outwardly. Consequently, the culture media and the cells are effectively mixed only in limited batches. It is often important for the cells and the cultural media to be exposed to the air. Since there is little vertical mixing, only the top most material in the flask is exposed to the air.

U.S. Pat. No. 3,622,129 is directed to a magnetic stirrer apparatus. A shaft extends through the bore of a closure in sealing relation therewith. A magnetic stirrer bar having a cylindrical shape is rotatably coupled to the shaft. The stirrer bar is pivoted on the shaft distal to the closure. Alternatively, the shaft and stirrer bar can be pivoted on the closure. A longitudinal adjustment of the shaft in the closure provides that the apparatus can be used with flasks of various sizes. The shaft and the stirrer bar are wholly encapsulated in a chemically inert plastic material, thereby avoiding contamination of the stirred matter. An external magnet magnetically engages the stirrer bar and causes it to rotate within the container. This results in a mixing of the material contained therein.

U.S. Pat. No. 4,355,906 is directed to a stirring apparatus for cell cultures. Substantially square blades with rounded corners are pivotally mounted to a central stirring assembly. A magnetic bar is also mounted to the stirring assembly. In operation, external magnets are rotated, thereby causing the magnetic bar mounted to the stirrer to rotate. The movement of the magnets on the stirrer causes the blades to rotate within the container and thereby causes the cell culture to be mixed.

U.S. Pat. No. 3,245,665 is directed to a magnetic mixing bar. The bottom of the bar is curved to approximate the shape of the bottom of the flask. Two magnetized rods are disposed in a bar. A rotating external magnet causes the bars in the rod to rotate. The use of two separate rods prevents the mixing bar from reversing polarity with the external magnet.

These references do not adequately address the problems solved by the instant invention, as one skilled in the art will appreciate from the following disclosure.

SUMMARY OF INVENTION

It is an object of an aspect of the instant invention to provide a mixing apparatus for agitating cells and cultural media efficiently and effectively without damaging the cells.

It is another object of an aspect of the instant invention to provide a mixing apparatus for agitating a liquid containing cells and a cultural media such that the liquid is moved both vertically and horizontally within a flask and the creation of dead spots is avoided.

It is another object of an aspect of the instant invention to provide a mixing apparatus for agitating a liquid containing cells and cultural media such that a large portion of the liquid is moved through cycles and is brought near the surface on a regular basis.

It is another object of an aspect of the invention to provide a mixing apparatus for agitating a liquid containing cells and cultural media such that the surface of the liquid is directly agitated, thus exposing larger portions of the liquid to the atmosphere on a regular basis.

It is another object of the invention to provide a flask with a larger opening, secured in several ways, such that the mixing apparatus can be more easily accommodated in the flask and such that more effective mixing can occur.

In accord with one aspect of the invention, an apparatus is provided for mixing a liquid culture media containing cells for a selected period of time at a controlled rate. A container has a substantially cylindrical wall, a top edge, a top opening defined by the top edge, a bottom surface distal to the top opening and a central axis extending from the top opening to the bottom surface. A baffle having a baffle surface and a baffle axis is mounted to an interior surface of the cylindrical wall. The baffle axis is substantially parallel to the central axis of the container. A hump having an apex is mounted on the bottom surface of the container. The central axis of the container extends through the apex of the hump. A top plate having a periphery and a center point is mounted to the top edge of the container at the periphery. A shaft is rotatably mounted to the top plate proximate the center point and extends along at least a portion of the central axis of the container. A paddle blade is fixedly mounted to the shaft and has an upper portion and a lower portion. The upper portion has outer edges which are parallel to the central axis of the container. The lower portion has side edges extending from the outer edges of the upper portion and slanting outward from the central axis near the bottom surface of the container. The bottom edge of the lower portion of the paddle blade extends closer to the bottom surface than the apex of the hump. A magnetic stir bar is rigidly mounted to the shaft distal to the top plate and disposed perpendicular to the paddle blade and parallel to the bottom surface.

In accord with another aspect of the invention, an apparatus for stirring liquids is provided. The apparatus includes a shaft rotatably mounted to a top plate. A blade is mounted to the shaft distal to the top plate and has an upper portion and a lower portion. The upper portion of the blade has a substantially trapezoidal shape with an inner edge, an outer edge, a top edge and a lower edge. The inner edge is fixedly attached to the shaft. The lower portion has a substantially trapezoidal shape with an upper edge and a bottom edge which are parallel. The upper edge of the lower portion extends contiguously along and is connected with the lower edge of the upper portion. The bottom edge is substantially longer than the upper edge. A magnetic stir bar is mounted to the shaft proximate the bottom edge of the lower portion and is disposed perpendicular to the blade.

In accord with another aspect of the invention, an apparatus for stirring liquids is provided having a liquid-tight container with a wall, an opening and a bottom surface. A shaft having a first end and a second end is rotatably mounted to the container at the first end. A blade having an upper portion and a lower portion is fixedly attached to the shaft proximate the second end. The upper portion has an inner edge, an outer edge, a top edge and a lower edge. The inner edge is attached to the shaft. The lower portion has an upper edge, a bottom edge, an inside edge, and an outside edge. The upper edge is contiguously and integrally formed with the lower edge of the upper portion. Further, the outside edge flanges away from the shaft, extending from the outer edge of the upper portion toward the bottom surface such that the bottom edge is longer than the upper edge.

In accord with another aspect of the invention, a method of agitating a liquid culture media containing cells for a selected period of time at a controlled rate is provided. A container is provided having an interior wall, a top edge, a top opening defined by the top edge, a bottom surface distal to the top opening. A shaft which is rotatably mounted within the container is also provided. A blade is fixedly mounted to one end of the shaft and disposed proximate the bottom surface. The blade has an upper portion with a substantially rectangular shape and a lower portion with a substantially trapezoidal shape which flanges outward near the bottom surface. A selected amount of liquid culture media is introduced to the container to a fluid level such that the fluid level of the liquid culture media rises to the upper portion of the blade and a section of the upper portion of the blade extends above the liquid level. The shaft is rotated at a controlled rate such that the blade moves through the liquid culture media. The liquid culture media is moved through a cycle from a position proximate the bottom surface to a position proximate the fluid level. The liquid culture media is aerated at the fluid level by moving the upper portion of the blade through, the surface of the liquid.

In accord with another aspect of the invention, an apparatus for closing and sealing an opening in a container is provided. A top plate has a profile larger than the opening such that the top plate cannot fit within the opening. The top plate also has a central axis extending through the top plate. A bottom plate has a periphery and a profile which is smaller than the opening such that the bottom plate can fit in the opening. The bottom plate is slidingly mounted to the top plate for controlled movement in a direction parallel to the central axis toward and away from the top plate. A beveled edge is disposed about the periphery of the bottom plate proximate the top plate. A flexible gasket disposed between the beveled edge of the bottom plate and the top plate. A mechanism is provided for displacing the bottom plate in a direction parallel to the central axis of the top plate and for securing the bottom plate at a fixed position with respect to the top plate.

DESCRIPTION OF PREFERRED EMBODIMENTS

Figure 1:
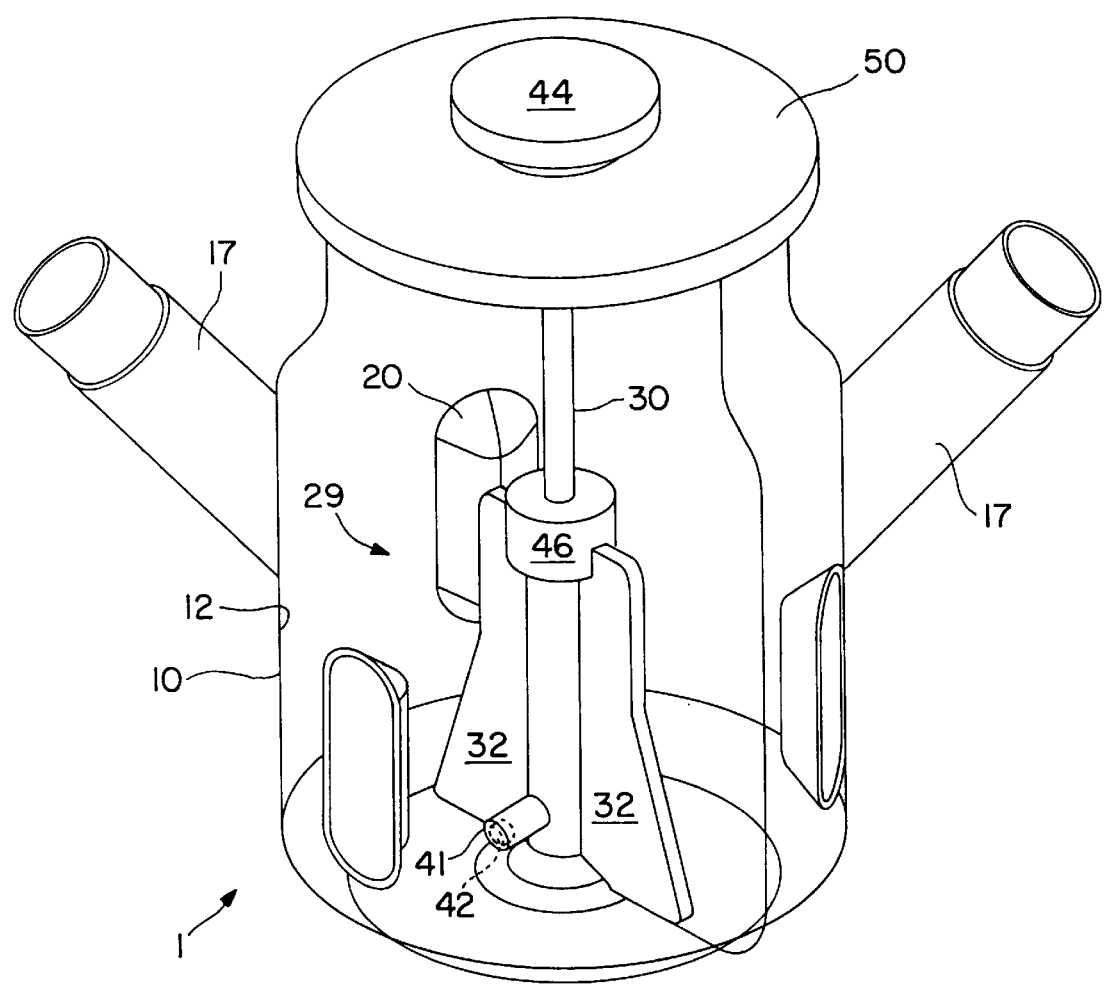
FIG. 1 is a front perspective view of a mixing apparatus in accord with an aspect of the invention.
Figure 3:
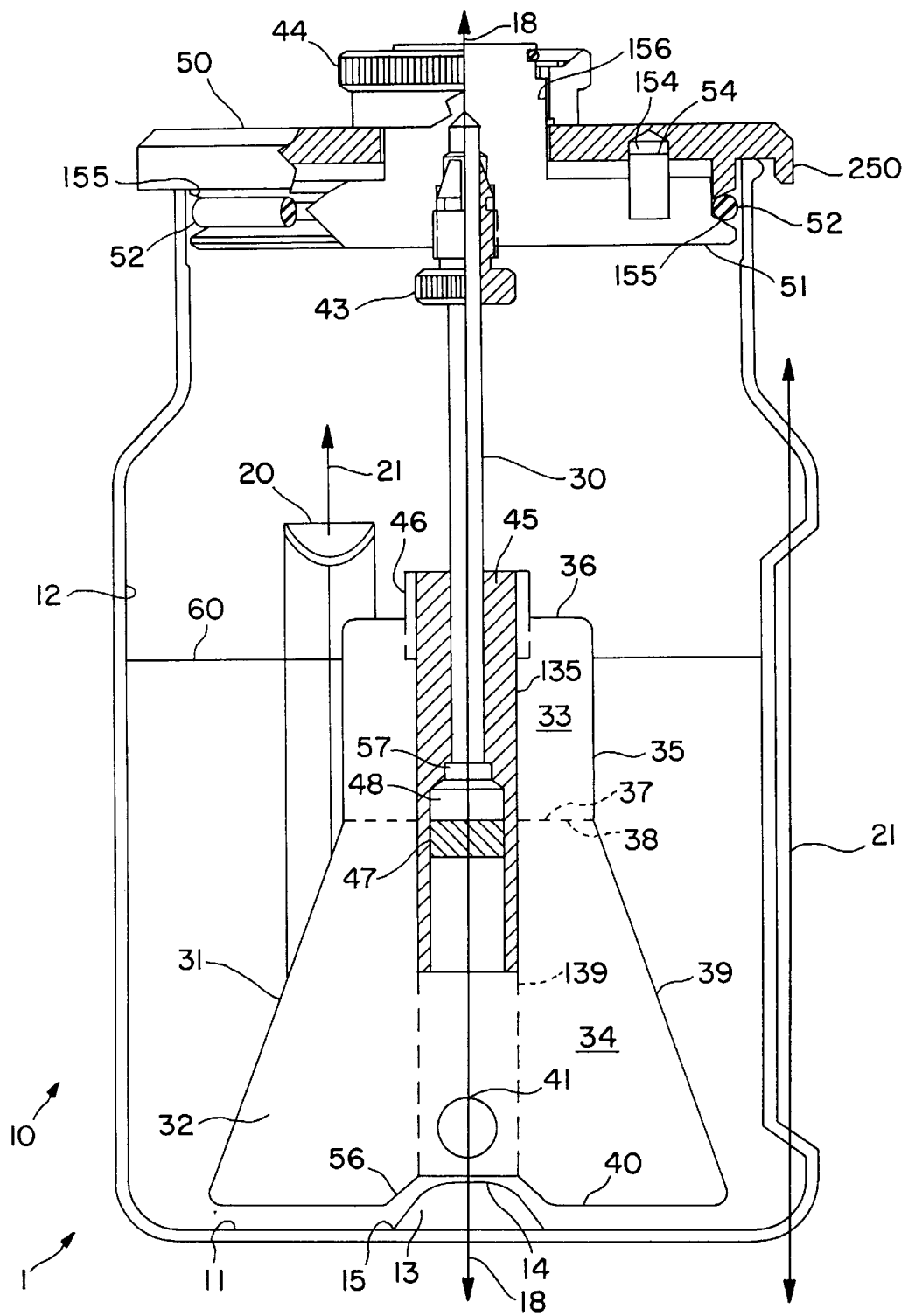
FIG. 3 is a side view in partial cutaway of the apparatus of FIG. 1, including a cultural media.

Referring to FIGS. 1 and 3, an apparatus 1 for mixing at least one liquid at a controlled rate is shown. AS currently intended, the apparatus is used to stir cells suspended in a culture media. The cells may also be attached to microcarrier beads suspended in the culture medium. This mixing can be performed over a relatively long time (i.e., from several hours up to several months) but must not produce great stress to cells suspended in the liquid. The mixing must be effective such that the liquid cycles from the bottom of the apparatus to the surface 60, and back again. Typically, the cells are maintained at about 27° C.–37° C. and mixed at 5 to 300 rpm. Of course, these conditions can be varied depending on the particular application.

A container 10 has a substantially cylindrical shape and a central axis 18. An interior wall 12 extends from the edge of a top opening 16 down to a bottom surface 11. Other than the baffles 20 (discussed below), the entire wall preferably provides a smooth cylindrical surface. The bottom surface is also preferably a smooth circular plate with the exception of the hump 13 (discussed below). The container may be made of glass or other acceptable non-reactive materials known in the art, such as polyethylene terephthalate or stainless steel.

As seen in FIG. 3, baffles 20 extend along the interior wall 12 in a vertical direction which is parallel to a central axis 18. Of course, the baffles can be angled, effectively spiraling up or down the interior wall, at any angle up to 90° with respect to the central axis. Each baffle has roughly the cross-sectional shape of a half-cylinder or an isosceles triangle and includes a baffle axis 21 which is substantially parallel to the central axis 18 (see FIG. 2). Each baffle includes a lead edge 22 and a trail edge 23 which are at a selected angle φ with respect to the interior wall 12. The angle φ of the lead edge and the trail edge are selected such that the flow of the liquid being mixed is of a turbulence sufficient to minimize the creation of large "dead spots" (i.e., areas where the liquid does not flow) in the flask. Preferably the lead edge and the trail edge are at about 120° to 130° with respect to the interior wall 12. It will be appreciated by one skilled in the art that the angle of the lead edge and the trail edge can be altered depending on the nature of the liquid to be mixed (viscosity, etc.) and the parameters of the apparatus for a particular operation (such as speed, etc.). Further, the baffles are preferably formed integrally with the wall of the container, forming a trough 420 at the container's exterior (which allows for easy gripping of the container). Of course, other structures, such as curved plates and the like, can be employed as baffles and still practice the invention. The baffles could also be angled or spiral-shape to direct the flow of the liquid or have an air-foil type profile.

Figure 2:
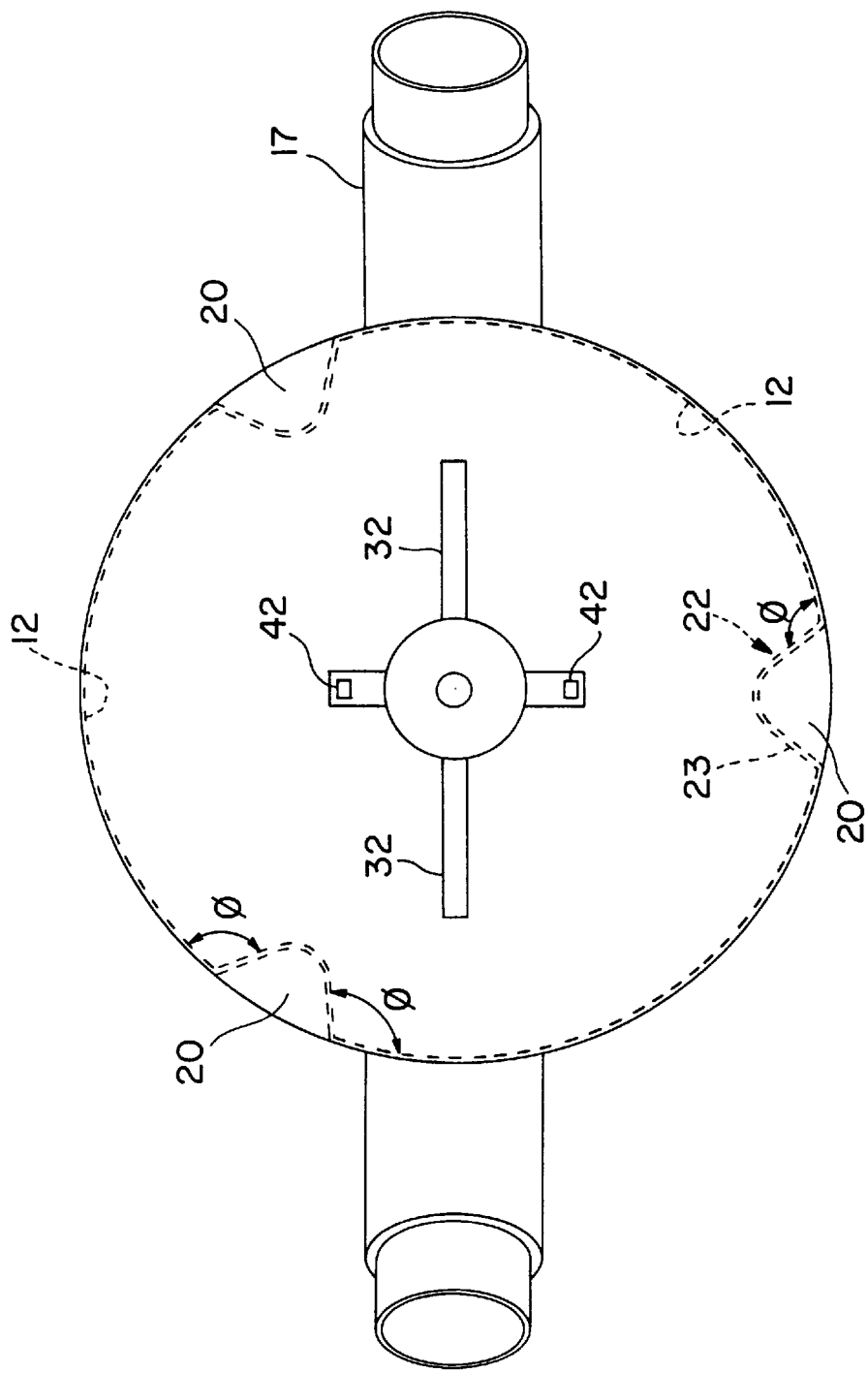
FIG. 2 is a top cut-away view of the apparatus on FIG. 1.

Preferably, there are three baffles 20 disposed symmetrically along the interior wall 12 about the central axis 18 (as seen in FIG. 2). of course, more or less baffles could be employed and still practice the invention.

The hump 13 is located at the center of the bottom surface 11 of the container 10. The hump has a peripheral edge 15 which forms a smooth curve with the bottom surface. Preferably the peripheral edge is at an angle of about 120° to 130°. The hump has the shape of a rounded cone having a substantially flat apex 14. The central axis 18 of the container 10 extends through the apex of the hump. Preferably the container, the baffles 20 and the hump are all integrally formed of a glass material. Other non-reactive materials can be employed, as one skilled in the art would appreciate, such as PET or stainless steel.

A stirring device 29 is positioned in the container 10. The stirring device includes a shaft 30 extending along the central axis 18. Referring particularly to FIG. 3, flange 48 is mounted to one end of the shaft. A hollow tube 45, called a bearing holder, is mounted to the shaft about the flange by a bearing 57. A plug 47 is positioned in the tube and abuts the flange, thereby securing the tube and the shaft together. The tube and the paddle 31 are free to rotate with respect to the shaft. Paddle 31 is mounted to the tube 45 by a retaining sleeve 46.

The paddle 31 preferably includes two flat blades 32 oriented at 180° with respect to each other (that is, they are coplanar). Each blade 32 includes an upper portion 33 and a lower portion 34 (see FIG. 2). The upper portion has a substantially rectangular shape. The inner edge 135 of the upper portion is positioned along the tube 45. The outer edge 35 of the upper portion extends substantially parallel to the central axis 18. The top edge 36 and the bottom edge 37 of the upper portion extend generally parallel to the bottom surface. Of course, the upper portion may also have more of a trapezoidal shape, depending on the particular application. The outer edge can be angled if desired to alter the flow characteristics.

The lower portion 34 of the blade 32 has a substantially trapezoidal shape. The inside edge 139 is positioned along the tube 45. The upper edge 38 of the lower portion is contiguous with the bottom edge 37 of the upper portion. Preferably, the side edge 39 of the lower portion flanges outward at an angle of about 70° to 80° from horizontal and extends downward toward the bottom surface to a point below the apex 14 of the hump 13. The angle of the side edge can be altered as appropriate when it is desired that the bottom edge 40 extend a greater or lesser distance to the interior wall 12. The bottom edge 40 of the lower portion 34 of the blade 32 is substantially parallel with the bottom surface (and is closer to the bottom surface than the apex of the hump) and is more than twice as long as the upper edge.

It will be appreciated that the blade can have various shapes (such as triangular) and practice the invention. Preferably, the outer edge of the blade angles outward toward the bottom. A notch 56 is disposed in the blade 32 along the lower edge 40 near the tube 45. The notch provides an accommodation for the hump 13, such that the lower edge of the lower portion 34 can rotate about the hump without interference. While the notch is a straight, angled edge, the notch could be curved to more closely emulate the profile of the hump, if desired.

A cylindrical plug or magnetic stir bar 41 is mounted on the bearing holder 45 proximate the lower edge 40 of the lower portion 34. Preferably the plug has a cylindrical shape, is disposed at 90° with respect to the blades 32 and is parallel to the bottom surface 11. Magnets 42 are disposed in the plug at its ends (that is, distal to the bearing holder 45). Of course, the plug may be a single magnetic rod, if desired. The plug, and the entire stirring device 29, should be covered by or formed from some non-reactive material, typically PTFE.

In one embodiment of the invention, the shaft 30 is mounted to a top plate 50 of 115–130 mm diameter by means of a shaft housing 43 and a shaft nut 44. The shaft housing prevents the shaft from rotating freely with respect to the housing. The shaft nut is threaded to the top plate, thereby securing the shaft housing and the shaft in position. Of course, other means for rotatably mounting the shaft to the top plate can be employed. Further, other means can be employed to rotate the shaft (such as an overhead direct drive mechanism) and still practice the invention.

Referring to FIG. 3, the top plate 50 is threaded at its peripheral wall 250 to the top opening 16. The top plate has a profile too large to fit through the top opening. A lower plate 51 is slidingly mounted to the top plate for movement in a direction parallel to the central axis 18. Registration pins 54 connected to the lower plate and disposed in channels 154 in the top plate align the lower plate for sealing in the top opening 16 of the container 10. A gasket 52 encircles beveled edges 155 on the top plate and the lower plate. The shaft nut 44 is operably connected to a screw member 156 on the lower plate 51, such that when the nut is turned, the lower plate is moved toward or away from the top plate. Internal friction between the nut and the screw member maintain the bottom plate and the top plate at a fixed orientation. The bottom plate has a profile sized to fit within the top opening. When the lower plate is moved toward the top plate, the gasket is squeezed between the beveled edges and forms a seal at the periphery 53 of the bottom plate and the top opening 16. Of course, other means for sealing the containers and maintaining the stirring device 29 in position can be employed and practice the invention. In this embodiment of the invention, the top plate can be placed on a top opening of any size, whether it is substantially smaller in size than the circumference of the container or the same circumference as the container.

To operate the system of the invention, liquid (such as a culture media including cells) is delivered through the top opening 16 of the container. Alternatively, liquid can be provided through a side portal 17. The liquid is added until it reaches a fluid level 60 (see FIG. 3) which is preferably below the top edge 36 of the upper portion 33 of the blades 32 and the top of the baffles 20 but above the upper edge 38 of the lower portion 34 of the blades 32. The top plate 50 is then positioned in the top opening 16 of the container 10 such that the shaft 30 of the stirring device 29 extends along the central shaft 18. A section of the upper portion of the blade extends above the fluid level.

The bottom plate 51 is positioned in the top opening 16 of the container 10. The top plate 50 is threaded to the outer edge of the container around the top opening. Once in place, the top nut 44 is turned, causing the bottom plate to be displaced toward the top plate. As a result, the gasket 52 is squeezed between the beveled edges and forced outward until it engages the side wall 12 of the container. The friction between the nut and the screw member of the bottom plate is adequate to maintain the plates in a fixed relative position.

Once the liquid is in the container 10 and the stirring device 29 is in place, an exterior magnet (not shown) is rotated, causing the magnetic stir bar 41 to spin within the container. As a result, the paddle 31 is also caused to rotate within the container. The rotation of the paddle causes the fluid to stir within the container. The shape of the blades 32 and the interaction with the baffles 20 causes the liquid to circulate from a position near the top of the fluid level 60 to a position near the bottom of the fluid level. The hump 13 prevents material from accumulating at the center of the bottom surface 11. Since the upper portion 33 of the blades 32 extend above the fluid level, the surface area of the liquid in the container is effectively increased, resulting in greater aeration of the liquid.

While this invention has been described with reference to specific embodiments disclosed herein, it is not confined to the details set forth and the patent is intended to include modifications and changes which may come within and extend from the following claims. In particular, the blades 32 can be curved rather than flat. Apertures can be provided in portions of the blade, and the baffles can be angled (rather than being parallel with the central axis 18) to alter the flow pattern of the fluid in the container 10. Further, additional blades can be provided as a particular designer desires. The entire blades can also bear other shapes (such as triangle or trapezoidal) but preferably a portion of the outer edge angles outward.

What is claimed is:

1. An apparatus for mixing a liquid culture media containing cells for a selected period of time at a controlled rate comprising:
   a container having a substantially cylindrical wall, a top opening at one end of the wall, a bottom surface distal to the top opening and a central axis extending from the top opening to the bottom surface;
   a baffle having a baffle surface and a baffle axis mounted to an interior surface of the cylindrical wall, wherein the baffle axis is substantially parallel to the central axis of the container;
   a hump having an apex, the hump being mounted on the bottom surface of the container, wherein the central axis of the container extends through the apex of the hump;
   a top plate having a peripheral wall, the top plate being mounted in the top opening of the container at the peripheral wall;
   a shaft mounted to the top plate and extending along at least a portion of the central axis of the container;
   a paddle rotatably mounted to the shaft and having an upper portion and a lower portion, the upper portion having outer edges, the lower portion having side edges extending from the outer edges of the upper portion and slanting outward from the central axis near the bottom surface of the container;
   wherein the bottom edge of the lower portion of the paddle extends closer to the bottom surface than the apex of the hump; and
   means for rotating the paddle about the central axis.

2. The apparatus of claim 1 wherein the paddle rotating means comprises a magnetic stir bar rigidly mounted to the paddle distal to the top plate and disposed perpendicular to the paddle and parallel to the bottom surface.

3. The apparatus of claim 1 wherein the top plate has a profile larger than the top opening of the container such that the top plate cannot fit within the opening, the apparatus further comprising:
   a bottom plate having a periphery and a profile which is smaller than the top opening of the container such that the bottom plate can fit in the top opening, the bottom plate being slidingly mounted to the top plate for controlled movement in a direction parallel to the central axis toward and away from the top plate;
   a beveled edge disposed about the periphery of the bottom plate proximate to the top plate;
   a flexible gasket disposed between the beveled edge of the bottom plate and the top plate;
   means for displacing the bottom plate in a direction parallel to the central axis; and
   means for securing the bottom plate at a fixed position with respect to the top plate.

4. The apparatus of claim 1 further comprising three baffles mounted to the interior surface of the cylindrical wall, the three baffles being equally spaced about the central axis with respect to each other and forming troughs at the exterior of the container for easy gripping.

5. The apparatus of claim 1 wherein the outer edges of the upper portion of the paddle are parallel to the central axis of the container and wherein the bottom edge of the lower portion of the paddle is parallel to the bottom surface of the container, the paddle further comprising a notch disposed in the paddle along the bottom edge proximate to the shaft.

6. The apparatus of claim 5 wherein the baffle comprises a lead edge and a trailing edge, wherein the lead edge forms a smooth, gentle curve with the interior surface of the container.

7. The apparatus of claim 5 wherein the baffle extends vertically upward to a height at least as high as a top edge of the upper portion of the paddle.

8. An apparatus for stirring liquids comprising:
   a top plate;
   a shaft mounted to the top plate;
   a container having an interior wall, a central axis, a bottom surface and a top opening, the top plate being disposed in the top opening and the shaft extending along the central axis;
   a blade mounted to the shaft distal to the top plate and having an upper portion and a lower portion;
   the upper portion of the blade having a substantially rectangular shape with an inner edge, an outer edge, a top edge and a lower edge, wherein the inner edge is adjacent to the shaft;
   the lower portion having a substantially trapezoidal shape with an upper edge and a bottom edge which are parallel, the upper edge of the lower portion extending contiguously along and connected with the lower edge of the upper portion, the bottom edge being substantially longer than the upper edge;
   the bottom surface of the container having located thereon an upwardly extending hump, the bottom edge of the lower portion of the blade extending below the apex of the hump so that the bottom surface of the container is spaced closer to the bottom edge of the lower portion of the blade than to the apex of the hump; and
   a means for rotating the blade.

9. The apparatus of claim 8 wherein the blade rotating means comprises a magnetic stir bar which is mounted to the shaft proximate the bottom edge of the lower portion and which is disposed perpendicular to the blade.

10. The apparatus of claim 8 wherein the top plate has a profile larger than the top opening of the container such that the top plate cannot fit through the top opening, the apparatus further comprising;
    a bottom plate having a periphery and a profile which is smaller than the top opening of the container such that the bottom plate can fit in the top opening, the bottom plate being slidingly mounted to the top plate for controlled movement in a direction parallel to the central axis toward and away from the top plate;
    a flexible gasket disposed between the bottom plate and the top plate near the periphery of the bottom plate; and
    means for displacing the bottom plate in a direction parallel to the central axis.

11. The apparatus of claim 8 wherein the container further comprises baffles mounted to the interior wall.

12. The apparatus of claim 8 wherein the bottom edge of the lower portion is more than twice as long as the upper edge of the lower portion.

13. An apparatus for stirring liquids comprising:

a liquid-tight container having a wall, an opening, an interior and a bottom surface;

a shaft having a first end and a second end, the first end being mounted to the container and the second end being disposed within the interior of the container;

a blade having an upper portion and a lower portion attached to the shaft proximate the second end;

a means for rotating the blade within the container at a controlled rate; and baffles mounted to the wall at the interior of the container;

the upper portion having an inner edge, an outer edge, a top edge and a lower edge, the inner edge being attached to the shaft; and the lower portion having an upper edge, a bottom edge, an inside edge, and an outside edge, the upper edge of the lower portion being contiguously and integrally formed with the lower edge of the upper portion, the outside edge of the lower portion flanging away from the shaft and extending from the outer edge of the upper portion toward the bottom surface of the container such that the bottom edge of the lower portion is longer than the upper edge of the lower portion.

14. The apparatus of claim 13 wherein the baffles are integrally formed with the wall of the container thereby creating a grip and the baffles extend in a substantially vertical direction, the apparatus further comprising a hump having an apex integrally formed with the bottom surface of the container.

15. The apparatus of claim 13 further comprising:

a top plate having a profile larger than the opening of the container such that the top plate cannot fit within the opening and having a central axis extending through the top plate;

a bottom plate having a periphery and a profile which is smaller than the opening of the container such that the bottom plate can fit in the opening, the bottom plate being slidingly mounted to the top plate for controlled movement in a direction parallel to the central axis toward and away from the top plate;

a flexible gasket disposed between the bottom plate and the top plate near the periphery of the bottom plate;

means for displacing the bottom plate in a direction parallel to the central axis; and means for securing the bottom plate at a fixed position with respect to the top plate.

16. A method of agitating a liquid culture media containing cells for a selected period of time at a controlled rate comprising:

providing a container having an interior wall, a top edge, a top opening defined by the top edge, a bottom surface distal to the top opening;

providing a shaft rotatably mounted within the container;

providing a blade fixedly mounted to one end of the shaft and disposed proximate the bottom surface, wherein the blade has an upper portion with a substantially rectangular shape and a lower portion with a substantially trapezoidal shape which flanges outward near the bottom surface;

introducing a selected amount of liquid culture media to the container to a fluid level such that the fluid level of the liquid culture media rises to the upper portion of the blade and a section of the upper portion of the blade extends above the liquid level;

rotating the shaft at a controlled rate such that the blade moves through the liquid culture media;

moving the liquid culture media through a cycle from a position proximate the bottom surface to a position proximate the fluid level; and aerating the liquid culture media at the fluid level by moving the upper portion of the blade through the liquid culture media at the fluid level and above the fluid level.

17. The method of claim 16 further comprising:

providing baffles along the interior wall of the container;

moving the liquid culture media over the baffles to increase mixing of the liquid culture media.

18. The method of claim 17 further comprising providing a magnetic stir rod fixedly mounted to the shaft wherein rotating the shaft includes rotating a magnetic bar exterior to the container which causes the magnetic stir rod to rotate.

* * * * *